(12) United States Patent
Altman

(10) Patent No.: US 12,728,549 B2
(45) Date of Patent: Sep. 8, 2026

(54) COVER CAP AND ASSEMBLY KIT CONSISTING OF COVER CAP AND BASE CAP

(71) Applicant: Digital Surgery Systems, Inc., Goleta, CA (US)

(72) Inventor: Steffi Altman, Donaueschingen (DE)

(73) Assignee: Aesculap AG, Tuttlingen (DE)

( * ) Notice: Subject to any disclaimer, the term of this patent is extended or adjusted under 35 U.S.C. 154(b) by 35 days.

(21) Appl. No.: 18/720,486

(22) PCT Filed: Dec. 16, 2022

(86) PCT No.: PCT/IB2022/062390
§ 371 (c)(1),
(2) Date: Nov. 22, 2024

(87) PCT Pub. No.: WO2023/111984
PCT Pub. Date: Jun. 22, 2023

(65) Prior Publication Data

US 2025/0381685 A1 Dec. 18, 2025

(30) Foreign Application Priority Data

Dec. 17, 2021 (DE) ......................... 102021133593.0

(51) Int. Cl.
*B25J 19/00* (2006.01)
*A61B 34/30* (2016.01)

(52) U.S. Cl.
CPC ........... *B25J 19/0075* (2013.01); *A61B 34/30* (2016.02)

(58) Field of Classification Search
CPC ..... B25J 19/0075; A61B 34/30; F16H 57/031
See application file for complete search history.

(56) References Cited

U.S. PATENT DOCUMENTS 6,279,413 B1 * 8/2001 Terada ................. B25J 19/0029 901/50
6,315,142 B1 * 11/2001 Kitamura ............ H04M 1/0252 220/326

(Continued)

FOREIGN PATENT DOCUMENTS

CN 108381535 A 8/2018
CN 212044733 U * 12/2020

(Continued)

OTHER PUBLICATIONS

Machine translation of CN-212044733-U, obtained from FIT database (Year: 2020).*

(Continued)

*Primary Examiner* — Thomas C Diaz
(74) *Attorney, Agent, or Firm* — K&L Gates LLP

(57) ABSTRACT

The present disclosure relates to a cover cap (2) for a medical component, in particular for a robotic arm, with a circular cylindrical tube section (4) that is closed at its one longitudinal end and is formed open at its other longitudinal end and has an edge (6) terminating the tube section (4) at the open longitudinal end, wherein the edge (6) lies in a plane inclined in relation to a tube section longitudinal axis, and at least three catch tabs (8, 10, 12) arranged at a distance from one another over the circumference of the tube section (4) and projecting radially inward from the edge (6) for attaching the cover cap (2) by clip-on connection. The present disclosure also relates to an assembly kit having such a cover cap (2) and a base cap (40) over which the cover cap (2) can be seated.

11 Claims, 3 Drawing Sheets

(56) References Cited

U.S. PATENT DOCUMENTS

| | | | | |
|---|---|---|---|---|
| D626,647 S * | 11/2010 | Amborn | D24/111 |
| 10,836,033 B2 | 11/2020 | Niu | |
| 11,623,681 B2 * | 4/2023 | Guerin | B62D 5/04<br>220/780 |
| 11,820,011 B2 * | 11/2023 | Caron | B25J 18/00 |

FOREIGN PATENT DOCUMENTS

| | | |
|---|---|---|
| WO | 2018/121711 A1 | 7/2018 |
| WO | 2023/111984 A1 | 6/2023 |

OTHER PUBLICATIONS

International Search Report and Written Opinion mailed Mar. 17, 2022 for International Application Serial No. PCT/IB2022/062390 filed on Dec. 16, 2022.

* cited by examiner

COVER CAP AND ASSEMBLY KIT CONSISTING OF COVER CAP AND BASE CAP

PRIORITY CLAIM

The present application is a national phase entry of PCT Patent Application No. PCT/IB2022/062390, filed on Dec. 16, 2022, which claims priority to and the benefit of German Patent Application No. 102021133593.0, filed on Dec. 17, 2021, the entirety of which are incorporated herein by reference.

TECHNICAL FIELD

The present disclosure relates to a (medical) covering cap for covering a medical component, in particular a robot arm. Moreover, the present disclosure relates to a construction kit having a base cap and such a covering cap.

BACKGROUND OF THE DISCLOSURE

From the prior art, it is known to cover medical products with components such as, for example, sealing caps, coverings, covers and the like for the purpose of protecting them from external media or mechanical stress. Covering caps used hitherto for robot arms do not offer sufficient protection against impact, and so, under corresponding stress, they can break into pieces and parts thereof can pass into the interior of the robot arm.

Furthermore, the covering caps used hitherto for robot arms are fixed to the robot arm by means of metals screws which are fitted in particular at an end face, in order, in this way, to ensure secure fastening. However, it has been shown that in particular the use of metal screws do not meet medical requirements if the latter are exposed to the surroundings. Therefore, metal screws have been replaced for example by nylon screws, having a silicone covering, these however having the disadvantage of significantly lower strength in comparison with metal screws.

In principle, it is possible, for avoiding contact between the surroundings and the metal screws, for screw-covering caps to be provided, said screw-covering caps being mounted individually onto each individual screw at the screw head thereof, for which purpose they are provided with engagement means, for example in the form of pins or mandrels, which are able to be brought into clamping engagement with a screw profile on the screw head (for example a cross-shaped-slot profile or Torx profile). However, this method is disadvantageous insofar as the screw-covering caps can fall off the screw heads and a large number of screw-covering caps have to be mounted, whereby production costs rise as a consequence of complex assembly.

The object of the present disclosure is therefore to provide a covering cap which is able to be mounted in a simple, reliable and cost-effective manner and which offers sufficient protection for the product covered by the covering cap.

SUMMARY OF THE DISCLOSURE

The object is achieved by a covering cap having the features of claim 1 and by a construction kit having the features of the alternative independent claim. Advantageous refinements are the subject matter of the dependent claims.

Accordingly, the covering cap has a circular-cylindrical tube portion (/sleeve portion) which is formed so as to be closed at its one longitudinal end and open at its other longitudinal end. At the open longitudinal end, the tube portion has an edge which terminates the tube portion, said edge lying in a plane which is inclined (/oblique) in relation to a tube-portion longitudinal axis. This means that the covering cap, according to its purpose of use, is of cup-shaped form and has an edge which is bevelled off (/bevelled) in relation to a cup longitudinal axis. In other words, the covering cap is not of rotationally symmetrical form.

The covering cap has at least three latching noses which are arranged so as to be distributed, and spaced apart from one another, over the circumference of the tube portion and which, for fastening of the covering cap in a clipping-on manner, that is to say for forming a snap-action connection with the component onto which the covering cap is able to be plugged, protrude from the edge radially inwards. In other words, the covering cap has individual radially projecting elevations, which are radially elastically displaceable, in order to enter into, or to release, a latching engagement, which is form-fitting/which to engage from behind in the longitudinal direction/axial direction, with a correspondingly formed counterpart component, which for example has three radially outwardly projecting projections to be engaged behind by the latching noses or has as an alternative a radially encircling projection to be engaged behind by the latching noses.

The fact that three latching noses are provided means that secure positioning of the covering cap via the latching engagement and easy-to-release fastening can be ensured, the cap being able to be mounted and dismounted without any tools and thus, in the event of the covering cap being damaged, being easy to replace. Moreover, the individual latching noses ensure that only a low expenditure of force is necessary to plug on the covering cap, since elastic deformation of the covering cap has to take place only at defined points, specifically at the latching noses, and not over the entire circumference. The circumferentially distributed arrangement of the latching ensures that the noses/snap-action hooks covering cap cannot be released inadvertently since, for release of the snap-action connection/latching engagement, a force has to be applied in a different direction to each of the three latching hooks, which, in comparison with an end-face fastening by means of screws, which can tear off if the dimensioning is too small, is advantageous.

The central concept of the disclosure is accordingly the provision of a covering cap suitable for medical use that is able to be plugged onto an already provided cap/base cap by means of three individual latching noses, which are arranged so as to be distributed over an oblique edge of the covering cap, in such a way that the covering cap is seated securely on the base cap and is at the same time able to be mounted or non-destructively dismounted without any tools and protects the base cap, arranged therebelow, in particular from mechanical stress.

According to a preferred embodiment, a first latching nose of the at least three latching noses may be arranged in a region of the edge that is spaced apart from the closed longitudinal end to the greatest extent in the longitudinal direction. This means that the first latching nose is formed in that region of the covering cap in which the tube portion, as seen in the longitudinal direction, is longer than in other regions of the covering cap or has the greatest length. In other words, the first latching nose may preferably be formed at a point of the covering cap that is outermost in the longitudinal direction. This has the advantage that plugging-on of the covering cap is facilitated in that the covering cap can be put on the component to be covered at its longer end, that is to say in the region of the first latching nose, and its shorter end can be swung/fitted over the component to be covered, whereby the latching engagement by way of the latching noses can be established particularly easily, that is to say with little expenditure of force.

According to a preferred embodiment, the three latching noses may be arranged so as to be distributed unevenly over the circumference of the tube portion. In particular, there is no latching nose arranged in a region of at least 30°, preferably 50°, particularly preferably of 90°, along the edge, which region is spaced apart from the closed longitudinal end to the smallest extent in the longitudinal direction, that is to say in a shorter tube portion of the covering cap as seen in the longitudinal direction. This facilitates the plugging-on of the covering cap. Moreover, a possible uneven introduction of force induced by the asymmetrical formation of the covering cap can be compensated by way of the uneven distribution of the latching noses.

According to a preferred embodiment, a second latching nose and a third latching nose of the at least three latching noses may be arranged so as to be spaced apart from the first latching nose to an equal extent, and may preferably be arranged so as to be offset from the first latching nose by 70° to 130° over the circumference of the edge. This means that the second and third latching noses are arranged symmetrically in relation to the first latching nose, whereby the mounting of the covering cap is facilitated. Preferably, the covering cap is formed so as to be overall axially symmetrical in relation to a centre of the first latching nose. In particular, the three latching noses, according to a first embodiment, may be arranged completely in one half of the edge 6, that is to say so as to be distributed over an angle range of at most 180°. Alternatively, the three latching noses, according to a second embodiment, may be arranged completely in three quarters of the edge 6, that is to say so as to be distributed over an angle range of at most 270°.

Alternatively or additionally, the second latching nose and the third latching nose, according to a refinement of the preferred embodiment, may be of identical form, and may in particular have the same width. This has the advantage that, when being mounted, the covering cap can be guided by the two latching noses and the forces can be introduced uniformly via the latching noses.

Alternatively or additionally, the second latching nose and/or the third latching nose, according to a refinement of the preferred embodiment, may have a smaller width than the first latching nose. In particular, the second latching nose and/or the third latching nose, according to a first embodiment, may have approximately 80 to 90% of the width of the first latching nose. Alternatively, the second latching nose and/or the third latching nose, according to a second embodiment, may preferably have 30% to 40% of the width of the first latching nose. In this case, it has turned out that a smaller difference in width is more advantageous if the second and third latching noses are arranged relatively close to the first latching nose or if the covering cap overall has a relatively small diameter.

According to a preferred embodiment, the at least three latching noses may protrude radially inwards to an equal extent, and may preferably protrude radially inwards by 1 to 2 mm. This has the advantage that a projection to be engaged behind by the latching noses may for example be formed so as to be continuous in the circumferential direction, so that, during the plugging-on, there is no need to ensure exact positioning in the circumferential direction. In this way, the assembly is further simplified.

According to a preferred embodiment, in the tube portion, there may be formed longitudinal slots which extend from the edge in the longitudinal direction of the tube portion in such a way that a radially elastically displaceable tab is formed between two respective longitudinal slots, at the free end of which tab a respective one of the at least three latching noses is arranged. In this way, it is possible for the latching noses to be formed so as to be radially elastically displaceable in a structurally simple manner, so that the functionality of the tool-free clipping-on is ensured.

According to a preferred embodiment, the covering cap may be constructed, preferably in one piece, from a glass-ball-reinforced or glass-fibre-reinforced plastic. In this case, the use of glass fibres results in greater strength than the use of glass balls, wherein, however, glass fibres promote greater warpage of the component. For example, the covering cap may be constructed from polyamide and have a glass-ball content of 30 to 70%, preferably of 40 to 60%, in particular of approximately 50%. Such a material selection has proven to be advantageous in particular with regard to its impact strength and to its breaking properties. A one-piece formation is suitable in particular regarding its ease of production from a plastic, so that it is necessary for only a single component, and not a large number of individual components, to be cleaned and/or sterilized, which, in particular for use in the medical sector, yields considerable advantages.

According to a preferred embodiment, the covering cap may be produced in an injection-moulding process. Consequently, it is possible for the shape of the covering cap to be designed in a relatively free manner and for the production to be simplified at the same time. Injection moulding is expedient in particular for the processing of glass-ball-reinforced or glass-fibre-reinforced plastics.

The object of the disclosure is also achieved by a construction kit for a medical component, in particular for a robot arm. The construction kit has the covering cap described and has a base cap, which base cap is preferably substantially circular-cylindrical in cross section and is preferably constructed from a plastic and has projecting, preferably a radially outwardly encircling collar. In particular, the base cap may have substantially the same shape as the covering cap, that is to say a bevelled cup shape, wherein the base cap is formed so as to be smaller than the covering cap so that the base cap is able to be covered completely by the covering cap, that is to say so that it is able to be arranged completely within the covering cap. In particular, the covering cap is able to be plugged onto the base cap in such a way that the at least three latching noses engage behind the collar. In other words, the construction kit has two caps able to be plugged onto one another that, by way of a snap-action connection, in the form of the latching noses engaging behind the collar, are able to be connected to one another.

According to a preferred embodiment, the base cap may have fastening openings which are arranged so as to be distributed in the circumferential direction and which serve for receiving (metal) screws for fastening to the robot arm, wherein, in a state of the covering cap in which it is plugged onto the base cap, the at least three latching noses are arranged so as to be offset from the fastening openings in the circumferential direction. This ensures that the latching noses are not arranged in the region of the (metal) screws, which could have an adverse effect on the electrostatic discharge of the construction kit.

In other words, the disclosure relates to a covering cap which consists of glass-ball-reinforced plastic and which can be plugged by hand onto a provided cap and which, with the aid of three latching noses, latches in place on said cap. In a standardized impact test, for measuring an appropriate mechanical strength, the plugged-on covering caps themselves are damaged but prevent damage to the cap arranged therebelow. These (plastic) caps and covering caps are installed, in particular at joints of robot arms, because the (plastic) caps alone are unable to pass the impact test. Moreover, the additional covering caps overcome the disadvantage of the (plastic) caps that, owing to the fastening thereof by metal screws, they become electrostatically charged and dirt can accumulate in the screw heads, it however being possible for the the metal screws, for this reason, to be replaced by nylon screws (having a silicone covering), said nylon screws not having sufficient strength. Consequently, according to the present disclosure, a covering cap composed of glass-ball-reinforced plastic, which can be produced in the desired colour for example in an injection-moulding process, is proposed. Covering caps of different size with (large/small) three respective latching noses make tool-free clipping onto the (plastic) caps possible. In this case, the latching noses are preferably positioned on the covering caps in such a way as not to be situated in the region of the screw connection of the caps.

DESCRIPTION OF EMBODIMENTS

Figures 1, 2, 3, 4, 5:
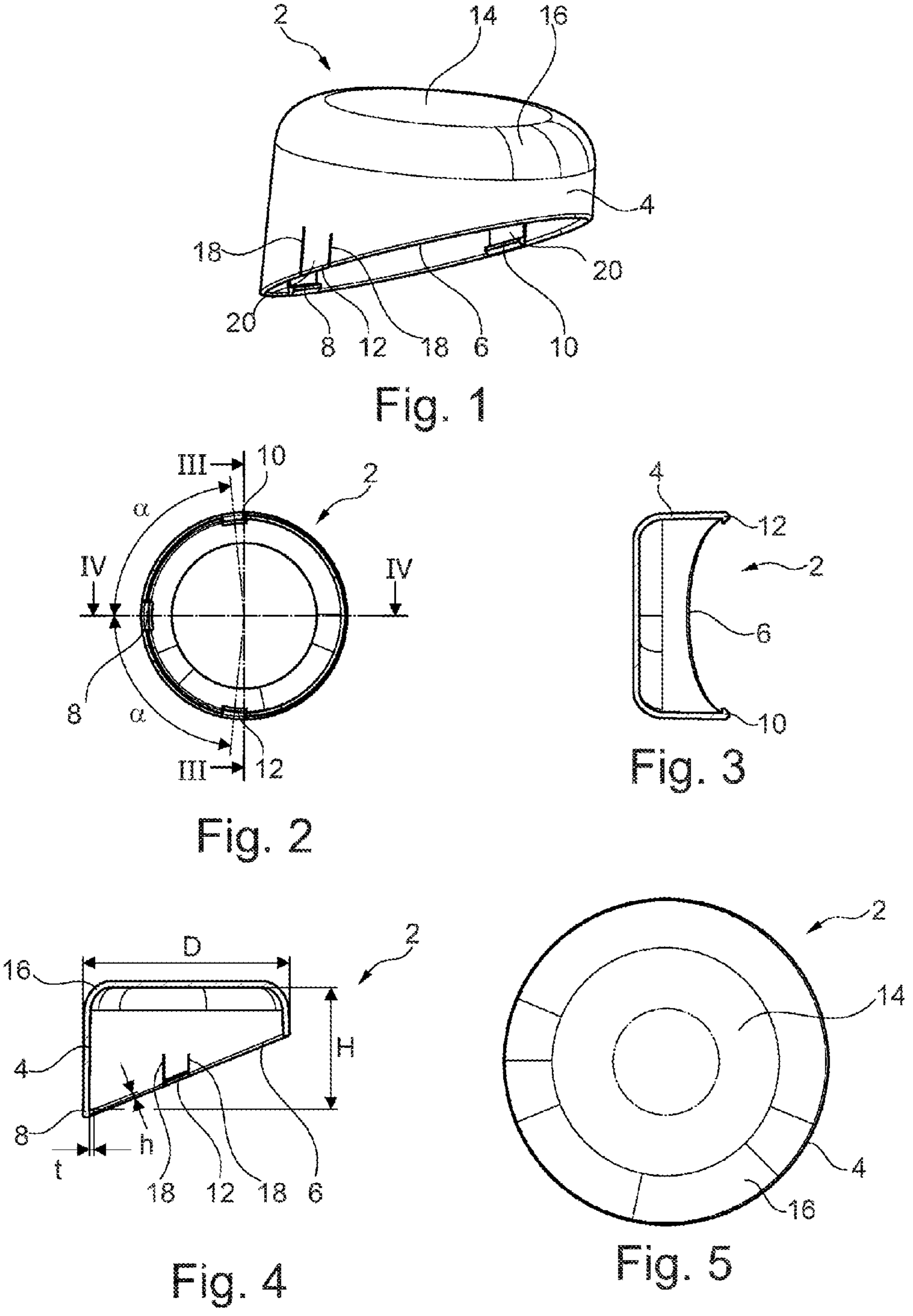
FIGS. 1 to 5 show different illustrations of a covering cap according to the disclosure in a first embodiment.
Figures 6, 7, 8, 9, 10:
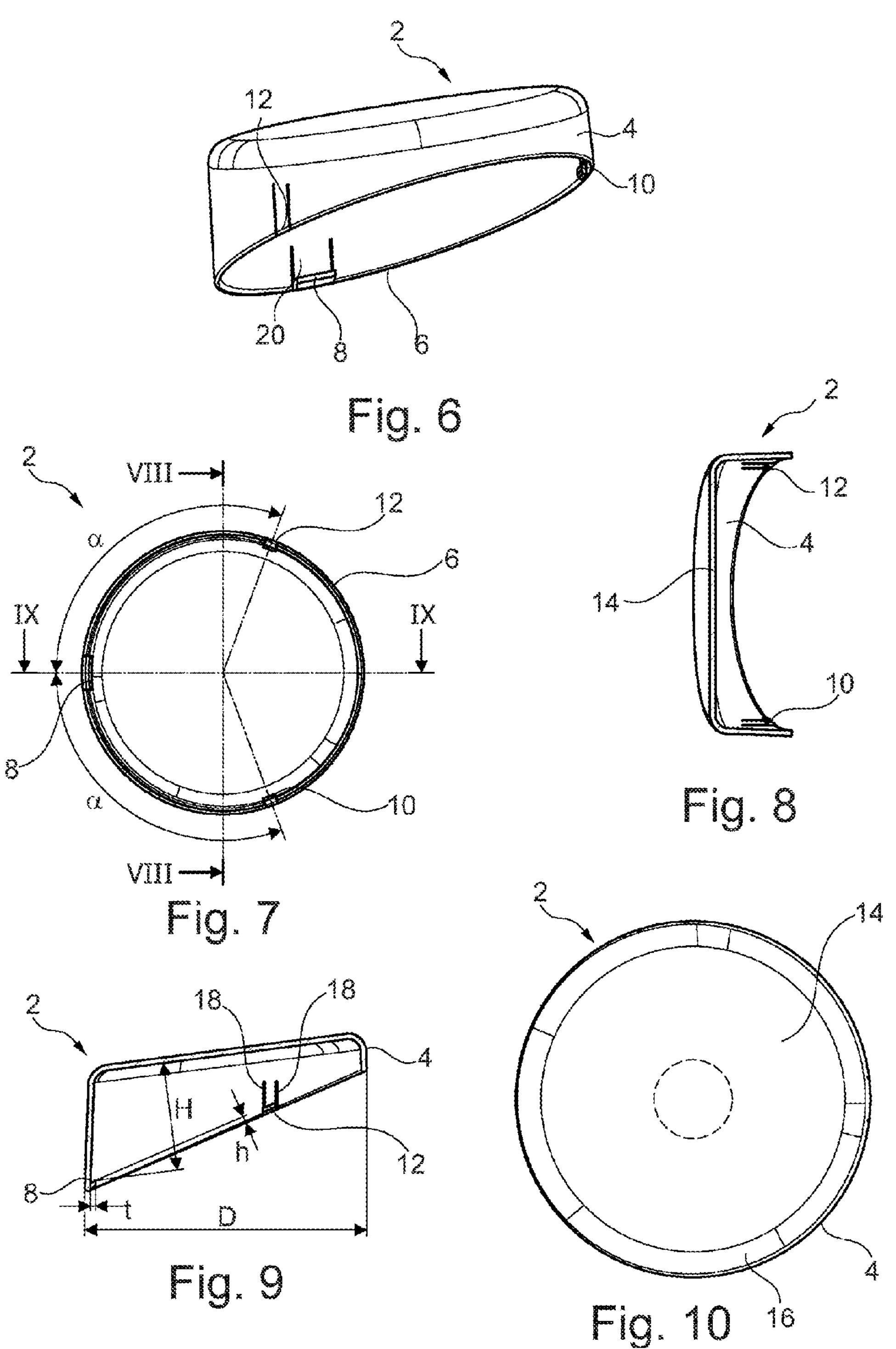
FIGS. 6 to 10 show different illustrations of a covering cap according to the disclosure in a second embodiment.

Embodiments of the present disclosure will be described below on the basis of the associated figures.

FIGS. 1 to 5 show different illustrations of a covering cap 2 according to the disclosure in a first embodiment. The covering cap 2 serves for covering a medical component, in particular a robot arm. The covering cap 2 has a circular-cylindrical tube portion 4 which is formed so as to be closed at its one longitudinal end and open at its other longitudinal end. The covering cap 2 is thus of substantially cup-shaped/pot-shaped form. At the open longitudinal end, the tube portion 4 has an edge 6 which terminates the tube portion. The edge 6 lies in a plane which is inclined/oblique in relation to a tube-portion longitudinal axis. This means that the covering cap 2 is formed so as to be not rotationally symmetrical but bevelled off/bevelled in relation to a cup longitudinal axis.

The covering cap 2 has at least three latching noses 8, 10, 12, which are also referred to below as a first latching nose 8, a second latching nose 10 and a third latching nose 12, and which are arranged so as to be distributed, and spaced apart from one another, over the circumference of the tube portion. The latching noses 8, 10, 12 protrude from the edge 6 radially inwards. The latching noses 8, 10, 12 serve for fastening of the covering cap 2 in a clipping-on manner.

The three latching grooves 8, 10, 12 are arranged so as to be distributed unevenly over the circumference of the edge 6. The first latching groove 8 is formed in an outermost region of the edge 6, that is to say on a circumferential portion of the tube portion 4 that is spaced apart from the closed longitudinal end to the greatest extent. The second latching groove 10 and the third latching groove 12 are arranged so as to be spaced apart from the first latching groove 8 to an equal extent in a circumferential direction, so that they are symmetrical in relation to the first latching groove 8. In the first embodiment, the first latching groove 8 and the second latching groove 10, and the first latching groove 8 and the third latching groove 12 include an angle $\alpha$, wherein the angle $\alpha$ is approximately 70° to 90°, for example approximately 84°. This means, too, that all three latching grooves 8, 10, 12 are arranged in one half of the covering cap 2, in particular that half of the covering cap 2 which extends to a greater extent in the longitudinal direction, that is to say in an angle range of at most 180°.

In the first embodiments, the first latching groove 8 has a greater width than the second and third latching grooves 10, 12, whose width is approximately 80 to 90% of the width of the first latching groove 8. The first latching groove 8 may have a width of 11 to 13 mm. The second latching groove 10 (and the third latching groove 12) may have a width of 9 to 11 mm.

Preferably, the three latching noses 8, 10, 12 may protrude radially inwards to an equal extent. For example, a depth t of the latching noses 8, 10, 12 may be 1 to 2 mm. For example, a height h of the latching noses 8, 10, 12 may be 1.5 to 2.5 mm, in particular approximately 2 mm. In the first embodiments, the covering cap 2 has a diameter D of 80 to 90 mm, in particular of approximately 84 mm. Moreover, the covering cap 2 has a height H of 45 to 55 mm, in particular of approximately 50 mm.

At its closed longitudinal end, the covering cap 2 has a cover portion 14 which is of substantially planar form and which transitions into the tube portion 4 via rounded edges 16.

Furthermore, in the tube portion 4, there are formed longitudinal slots 18 which extend from the edge 6 in the longitudinal direction of the tube portion 4 in such a way that a radially elastically displaceable tab 20 is formed between two respective longitudinal slots 18. In this case, a respective one of the at least three latching noses 8, 10, 12 is formed at a free end of a respective tab 20.

FIGS. 6 to 10 show different illustrations of the covering cap 2 according to the disclosure in a second embodiment. The second embodiment corresponds substantially to the first embodiment, and so only the differences between the first and second embodiments will be discussed below.

In the second embodiment, the angle $\alpha$ included between the first latching groove 8 and the second latching groove 10, and between the first latching groove 8 and the third latching groove 12 is approximately 100° to 130°, for example approximately 110°. This means that all three latching grooves 8, 10, 12 are arranged in two thirds to three quarters of the covering cap 2, in particular of that circumferential portion of the covering cap 2 which extends to a greater extent in the longitudinal direction, that is to say in an angle range of at most 240° to 270°.

In the second embodiments, the first latching groove 8 has a greater width than the second and third latching grooves 10, 12, whose width is approximately 30 to 50% of the width of the first latching groove 8. The first latching groove 8 may have a width of 14.5 to 16.5 mm. The second latching groove 10 (and the third latching groove 12) may have a width of 5 to 7 mm.

In the second embodiments, the depth t of the latching noses 8, 10, 12 is 1 to 2 mm and the height h of the latching noses 8, 10, 12 is 2.5 to 3.5 mm, in particular approximately 3 mm. In the second embodiments, the covering cap 2 has a diameter D of 120 to 130 mm, in particular of approximately 125 mm. Moreover, the covering cap 2 has a height H of 45 to 55 mm, in particular of approximately 48 mm.

Figure 11:
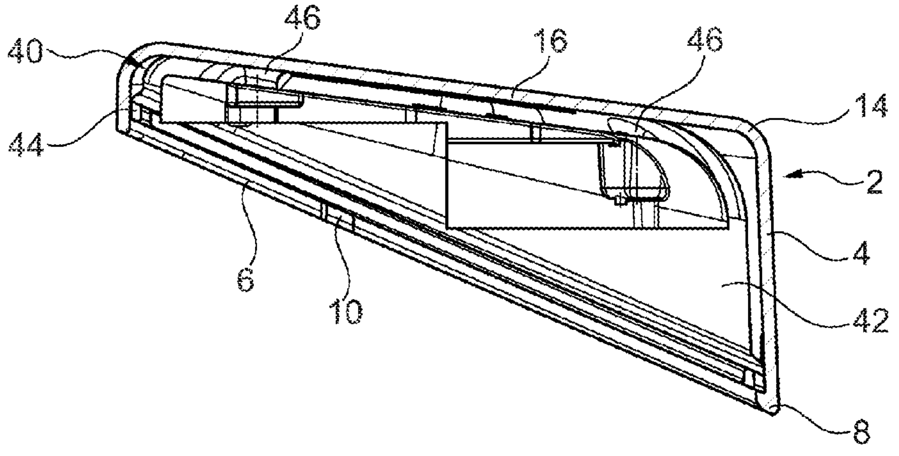
FIG. 11 shows a longitudinal-section illustration of a construction kit according to the disclosure with the covering cap and with a base cap.

FIG. 11 shows a longitudinal-section illustration of a construction kit according to the disclosure having a covering cap 2 and having a base cap 40.

The base cap 40 is preferably of substantially circular-cylindrical form in cross section. The base cap 40 preferably be constructed from a plastic. The base cap 40 may have substantially the same shape as the covering cap 2, that is to say a bevelled cup shape. This means that a tube portion 42 of the base cap 40 is bevelled, so that an edge delimiting the tube portion 42 lies in a plane which that is inclined, is to say not perpendicular, in relation to the longitudinal axis of the base cap 40. In particular, the base cap 40 may be formed so as to be smaller than the covering cap 2 so that the base cap 40 is able to be covered completely by the covering cap 2, that is to say so that it is able to be arranged completely within the covering cap 2.

The base cap 40 has a radially outwardly projecting, preferably encircling collar 44. In particular, the covering cap 2 is able to be plugged onto the base cap 40 in such a way that the at least three latching noses 8, 10, 12 engage behind the collar 44. In other words, the construction kit has two caps 2, 40 able to be plugged onto one another that, by way of a snap-action connection, in the form of the latching noses 8, 10, 12 engaging behind by the collar 44, are able to be connected to one another.

Moreover, the base cap 44 may have fastening openings 46 which are arranged so as to be distributed (evenly) circumferential direction and which serve for receiving (metal) screws for fastening to the medical component to be covered, in particular to the robot arm. In this case, the construction kit is formed/mounted/assembled in such a way that, in a state of the covering cap 42 in which it is plugged onto the base cap 40, the at least three latching noses 8, 10, 12 are arranged so as to be offset from the fastening openings 46 in the circumferential direction.

The invention claimed is:

1. A cover cap for covering a medical component, the cover cap including:

a circular-cylindrical tube section that is closed at one longitudinal end and open at its other longitudinal end;

an edge that lies in a plane inclined to a pipe section longitudinal axis; and at least three latching lugs distributed over a circumference of the circular-cylindrical tube section and arranged at a distance from one another, the at least three latching lugs being configured to protrude radially inwards from the edge for clipping the cover cap to the medical component, wherein a first latching lug of the at least three latching lugs is arranged in a region of the edge that is furthest from the closed end, and wherein a second latching lug and a third latching lug of the at least three latching lugs are arranged equidistant from the first latching lug.

2. The cover cap of claim 1, wherein the medical component is a robotic arm.

3. The cover cap of claim 1, wherein the cover cap is constructed in one piece from a glass bead or glass fiber reinforced plastic.

4. The cover cap of claim 1, wherein the second latching lug and the third latching lug are of identical design and have a same width.

5. The cover cap of claim 1, wherein the second latching lug or the third latching lug have a smaller width than the first latching lug.

6. A cover cap for covering a medical component, the cover cap including:

a circular-cylindrical tube section that is closed at one longitudinal end and open at its other longitudinal end;

an edge that lies in a plane inclined to a pipe section longitudinal axis; and at least three latching lugs distributed over a circumference of the circular-cylindrical tube section and arranged at a distance from one another, the at least three latching lugs being configured to protrude radially inwards from the edge for clipping the cover cap to the medical component, wherein a first latching lug of the at least three latching lugs is arranged in a region of the edge that is furthest from the closed end, and wherein a second latching lug and a third latching lug of the at least three latching lugs are arranged along the circumference of the edge and offset by 70° to 130° from the first latching lug.

7. The cover cap of claim 6, wherein the at least three latching lugs are arranged unequally distributed over the circumference of the circular-cylindrical tube section.

8. A cover cap for covering a medical component, the cover cap including:

a circular-cylindrical tube section that is closed at one longitudinal end and open at its other longitudinal end;

an edge that lies in a plane inclined to a pipe section longitudinal axis; and at least three latching lugs distributed over a circumference of the circular-cylindrical tube section and arranged at a distance from one another, the at least three latching lugs being configured to protrude radially inwards from the edge for clipping the cover cap to the medical component, wherein longitudinal slots are formed in the circular-cylindrical tube section and extend from the edge in the longitudinal direction of the circular-cylindrical tube section in such a way in that between each two longitudinal slots a tab is formed that is displaced elastically in a radial direction and at the free end of which one of the at least three latching lugs is arranged.

9. The cover cap of claim 8, wherein the cover cap is constructed in one piece from a glass bead or glass fiber reinforced plastic.

10. A kit for a medical component, the kit including:

a cover cap for covering the medical component, the cover cap including:

a circular-cylindrical tube section that is closed at one longitudinal end and open at its other longitudinal end, an edge that lies in a plane inclined to a pipe section longitudinal axis, and at least three latching lugs distributed over a circumference of the circular-cylindrical tube section and arranged at a distance from one another, the at least three latching lugs being configured to protrude radially inwards from the edge for clipping the cover cap to the medical component; and a base cap that has a circular-cylindrical cross-section, the base cap being constructed from a plastic and having a radially outward protruding collar, wherein the cover cap is configured to be pushed onto the base cap in such a way that the at least three latching lugs engage the radially outward protruding collar.

11. The kit according to claim 10, wherein the base cap includes fastening openings distributed in a circumferential direction for receiving screws for fastening to the medical component, and wherein the at least three latching lugs of the cover cap are offset in the circumferential direction in relation to the fastening openings.

* * * * *